United States Patent
Rozet et al.

(10) Patent No.: US 11,667,913 B2
(45) Date of Patent: *Jun. 6, 2023

(54) METHODS FOR PERFORMING ANTISENSE OLIGONUCLEOTIDE-MEDIATED EXON SKIPPING IN THE RETINA OF A SUBJECT IN NEED THEREOF

(71) Applicants: INSERM (INSTITUT NATIONAL DE LA SANTE ET DE LA RECHERCHE MEDICALE), Paris (FR); FONDATION IMAGINE, Paris (FR); UNIVERSITE PARIS DESCARTES, Paris (FR); ASSISTANCE PUBLIQUE-HOPITAUX DE PARIS (APHP), Paris (FR)

(72) Inventors: Jean-Michel Rozet, Paris (FR); Isabelle Perrault, Paris (FR); Xavier Gerard, Paris (FR); Josseline Kaplan, Paris (FR); Arnold Munnich, Paris (FR)

(73) Assignees: INSERM, Paris (FR); FONDATION IMAGINE, Paris (FR); UNIVERSITE PARIS CITE, Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,477

(22) PCT Filed: Jul. 8, 2014

(86) PCT No.: PCT/EP2014/064604
§ 371 (c)(1),
(2) Date: Jan. 7, 2016

(87) PCT Pub. No.: WO2015/004133
PCT Pub. Date: Jan. 15, 2015

(65) Prior Publication Data
US 2016/0150555 A1   May 26, 2016
US 2019/0037583 A2   Jan. 31, 2019

(30) Foreign Application Priority Data

Jul. 8, 2013 (EP) .................................. 13305968

(51) Int. Cl.
C12N 15/113   (2010.01)
A61K 48/00    (2006.01)
C12N 15/11    (2006.01)

(52) U.S. Cl.
CPC .......... *C12N 15/111* (2013.01); *C12N 15/113* (2013.01); *C12N 2310/11* (2013.01);
(Continued)

(58) Field of Classification Search
CPC ............ C12N 15/113; C12N 2310/315; C12N 2310/321; C12N 2310/11; C12N 2320/33; H04L 43/0882
See application file for complete search history.

(56) References Cited

U.S. PATENT DOCUMENTS

2008/0268051 A1* 10/2008 Hughes ................ A61K 9/0048
514/1.1
2009/0285840 A1* 11/2009 Blobel .................. C07K 16/40
424/178.1

FOREIGN PATENT DOCUMENTS

EP   2 718 437 B1   5/2018
WO   2012/145601 A2  10/2012
(Continued)

OTHER PUBLICATIONS

Gerard, et al. Aon-Mediated Exon Skipping Restores Ciliation in Fibroblasts Harboring the Common Leber Congenital Amaurosis CEP290 Mutation. Molecular Therapy—Nucleic Acids, v.1, e29 (Jun. 2012).*

(Continued)

*Primary Examiner* — Terra C Gibbs
(74) *Attorney, Agent, or Firm* — WC&F IP

(57) ABSTRACT

The present invention relates to methods for performing antisense oligonucleotide-mediated exon skipping in the retina of a subject in need thereof. In particular, the present invention relates to a method for performing antisense oligonucleotide-mediated exon skipping in a retina cell of a (Continued)

Figure 1:
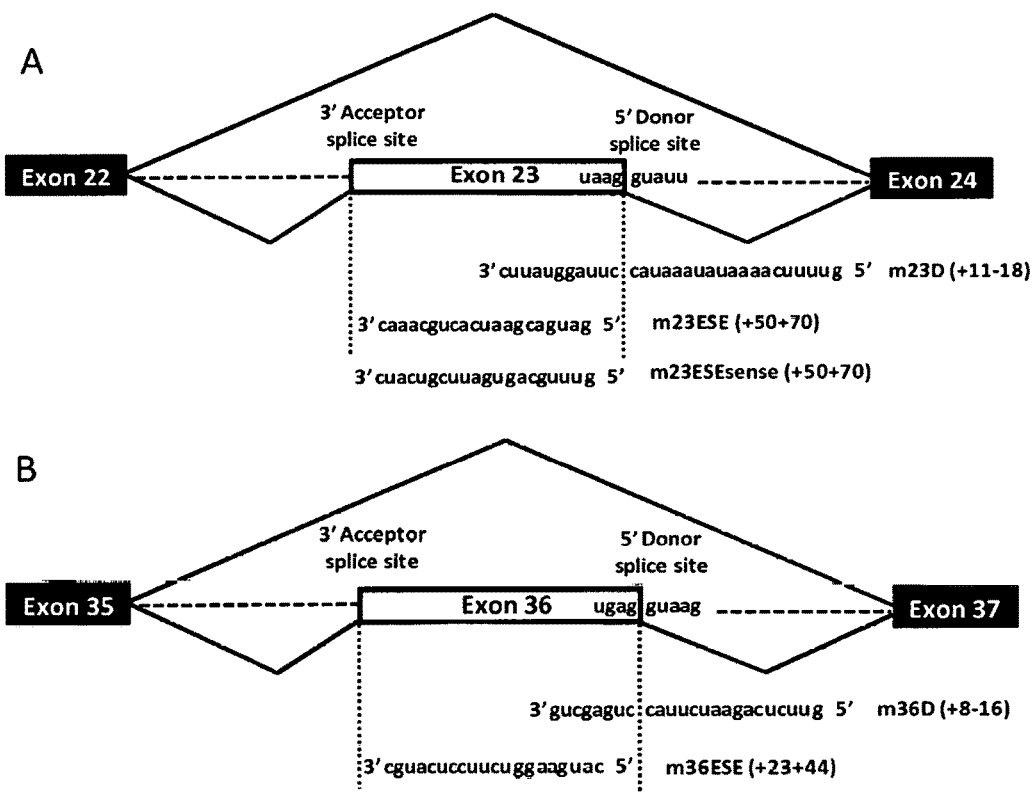

subject comprising the step of injecting into the vitreous of the subject an amount of the antisense oligonucleotide.

9 Claims, 4 Drawing Sheets

Specification includes a Sequence Listing.

(52) U.S. Cl.
CPC .. *C12N 2310/315* (2013.01); *C12N 2310/321* (2013.01); *C12N 2310/3521* (2013.01); *C12N 2320/33* (2013.01)

(56) References Cited

FOREIGN PATENT DOCUMENTS

| | | |
|---|---|---|
| WO | 2012/168435 A1 | 12/2012 |
| WO | 2013/036105 A1 | 3/2013 |

OTHER PUBLICATIONS

Perrault, et al. (2007) Hum. Mutat., vol. 28(4): 416-416. doi:10.1002/humu.9485. (Year: 2007).*
Northeast Wisconsin Retina Associates [online]. [retrieved on Jul. 1, 2019]. Retrieved from the Internet: <http://newretinamd.com/surgical_procedures/intraocular_injections.php>. (Year: 2019).*
De Kozak, et al. (2004) "Intraocular injection of tamoxifen-loaded nanoparticles: a new treatment of experimental autoimmune uveoretinitis." European Journal of Immunology, vol. 34:3702-12. (Year: 2004).*
Rakoczy, P. E., Lai, M. C., Watson, M., et al. (1996) Targeted delivery of an antisense oligonucleotide in the retina. Uptake, distribution, stability and effect. Antisense Nucleic Acid Drug Dev. 6, 207-213. Only Abstract attached.*
Shen, WY, Garrett, KL, da Cruz, L, Constable, IJ and Rakoczy, PE (1999). Dynamics of phosphorothioate oligonucleotides in normal and laser photocoagulated retina. Br J Ophthalmol 83: 852-861.*
Garanto et al. (HMG Advance Access published Apr. 22, 2016).*
Gerard et al. (Molecular Therapy—Nucleic Acids, 2015 4, e250).*
Collin et al., "Antisense Oligonucleotide (AON)-based Therapy for Leber Congenital Amaurosis Caused by a Frequent Mutation in CEP290", Molecular Therapy—Nucleic Acids, Mar. 1, 2012, p. e14, vol. 1, No. 3.
Piroska et al., "Targeted delivery of an antisense oligonucleotide in the retina: uptake, distribution, stability, and effect", Antisense and Nucleic Acid Drug Development, 1996, pp. 207-213, vol. 6, No. 3.
Bochot et al., "Intravitreal administration of antisense oligonucleotides: Potential of liposomal delivery", Progress in Retinal and Eye Research, Mar. 2000, pp. 131-147, vol. 19, No. 1.
Andrieu-Soler et al: "Single-stranded oligonucleotide-mediated in vivo gene repair in the rd1 retina", Molecular Vision, vol. 13, pp. 692-706, May 2, 2007.
Uehara et al: "Dual suppresion of hemangiogenesis and lymphangiogenesis by splice-shifting morpholinos targeting vasuclar endothelial growth factor reepetor 2 (KDR)", The FASEB Journal, vol. 27, pp. 1-10, Jan. 2013.
Rivera et al: A comprehensive Survey of sequence Variation in the AVCA4 (ABCR) Gene in Stargardt Disease and Age-Related Macular Degeneration, American Journal of Human Genetics, vol. 67, pp. 800-813, 2000.
Anand et al: "Cilliary Transition Zone (TZ) Proteins RPGR and CEP290: Role in Photoreceptor Cilia and Degenerative Diseases" Expert Opin Ther Targets, vol. 16, No. 6, pp. 541-551, Jun. 2012.
Cideciyan et al: "ABCA4 disease progression and a proposed strategy for gene therapy", Human Molecular Genetics, vol. 18, No. 5, pp. 931-941, 2009.

Cideciyan et al: "Cone photoreceptors are the main targets for gene therapy of NPHP5 (IQCB1) or NPHP6 (CEP290) blindness: generation of an all-cone Nphp6 hypomorph mouse that mimics the human retinal ciliopathy", Human Molecular Genetics, vol. 20, No. 7, pp. 1411-1423, 2011.
Fattal et al: "Ocular delivery of nucleic acids: antisense oligonucleotides, aptamers and siRNA", Advanced Drug Delivery Reviews, vol. 58, pp. 1203-1223, 2006.
Gomes Dos Santos et al: "Intraocular Delivery of Oligonucleotides", Current Pharmaceutical Biotechnology, vol. 7, pp. 7-15, 2005.
Han et al: "DNA nanoparticle-mediated ABCA4 delivery rescues Stargardt dystrophy in mice", The Journal of Clinical Investigation, vol. 122, No. 9, pp. 3221-3226, 2012.
Hocine et al: "RNA Processing and Export", Cold Spring Harbor Perspectives in Biology, 2010.
Jazayeri et al: Identification and Characterization of Antisense Oligonucleotides (ASOs) Directed at Mouse Rhodopsin, a Gene Specifically Expressed in the Photoreceptor Cells, 2013.
Lamber et al: "Laser-induced choroidal neovascularization model in mice", 2013.
Lenis et al: "Expression of ABCA4 in the retinal pigment epithelium and its implications for Stargardt macular degeneration", PNAS, vol. 115, No. 47, pp. E11120-E11127, 2018.
Rachel et al: "Photoreceptor sensory cilia and ciliopathies: focus on CEP290, RPGR and their interacting protiens", Cilia, vol. 1, No. 22, 2012.
Shah et al: "Acanthocytosis", NCBI Bookshelf, 2020.
Wang et al: "Proteomic evidence that ABCA4 is vital for traumatic proliferative vitreoretinopathy formation and development", Experimental Eye Research, Feb. 5, 2019.
Behar-Cohen et al: "Anatomy of the retina", Med Sci, pp. 594-599, vol. 36, No. 6-7, Jul. 2, 2020.
Behar-Cohen: Declaration, May 30, 2021.
Brancati et al: "CEP290 Mutations Are Frequently Identified in the Oculo-Renal Form of Joubert Syndrome-Related Disorders", The American Journal of Human Genetics, vol. 81, pp. 104-113, Jul. 2007.
Brown et al: "Chromatin and epigenetic regulation of pre-mRNA processing", Human Molecular Genetics, vol. 21, pp. R90-R96, Aug. 29, 2012.
Cideciyan et al: Durable vision improvement after a single treatment with antisense oligonucleotide sepofarsen: a case report, Nature Medicine, vol. 27, pp. 785-789, May 2021.
Crooke et al: "Cellular uptake and trafficking of antisense oligonucleotides", Nature Biotechnology, vol. 35, No. 3, pp. 230-238, Mar. 2017.
Lenis et al: "Expression of ABCA4 in the Retinal Pigment Epithelium and its Implications for Stargardt Macular Degeneration".
Leroy et al: "Leber Congenital Amaurosis due to CEP290 Mutations-Severe Vision Impairment with a High Unmet Medical Need", RETINA, vol. 41, No. 5, pp. 898-907, May 1, 2021.
Murray et al: "Allele-Specific Inhibition of Rhodopsin With an Antisense Oligonucleotide Slows Photoreceptor Cell Degeneration", Biochemistry and Molecular Biology, vol. 56, No. 11, pp. 6362-6375, Oct. 2015.
Youtube video of retina dissection available at https://www.youtube.com/watch?v=2QI2oMYi8dg, Dec. 10, 2010.
WHO Drug Information, vol. 34, No. 1, 2020.
Witmer et al: "Expression of Vascular Endothelial Growth Factor Receptors 1, 2, and 3 in Quiescent Endothelia", The Journal of Histochemistry & Cytochemistry, vol. 50, No. 6, pp. 767-777, 2002.
Hu et al., "VEGF as a Direct Functional Regulator of Photoreceptors and Contributing Factor to Diabetes-Induced Alteration of Photoreceptor Function", Biomolecules 2021, 11, 988.
Juliano et al., "Cellular Uptake and Intracellular Trafficking of Antisense and siRNA Oligonucleotides", Bioconjug Chem. Feb. 15, 2012; 23(2): 147-157.

* cited by examiner

METHODS FOR PERFORMING ANTISENSE OLIGONUCLEOTIDE-MEDIATED EXON SKIPPING IN THE RETINA OF A SUBJECT IN NEED THEREOF

FIELD OF THE INVENTION

The present invention relates to methods for performing antisense oligonucleotide-mediated exon skipping in the retina of a subject in need thereof.

BACKGROUND OF THE INVENTION

The human genome consists of 20,000 to 25,000 protein coding genes, but the repertoire of mRNA sequences and encoded proteins is far greater as a result of multiple RNA isoforms generated from each gene. RNA transcript diversity evolves from several mechanisms, but RNA alternative splicing represents a major factor driving phenotypic diversity in higher eukaryotes. Indeed splicing events are highly prevalent, estimated to occur for 95% of all multiexon genes. There are numerous modes of RNA alternative splicing observed, of which the most common is exon skipping. In this mode, a particular exon may be included in mRNAs under some conditions or in particular tissues, and omitted from the mRNA in others. The majority of splicing events alter the encoded protein, more than half causing a shift in the mRNA reading frame. Common genetic variants can afford changes in alternative splicing within a "normal" physiological range. However, abnormal variations in splicing are implicated in a large proportion of human genetic disorders, and in particular retinal diseases; more up to 50% of diseases with genetic components involve splicing mutations. Mutations causing aberrant splicing typically result in nonfunctional protein or nonsense-mediated RNA decay, if a codon phase shift introduces premature termination signals.

Mutations in genes specific to the inner retinal layer can result in inherited retinal diseases (IRDs) e.g. congenital stationary night blindness (bipolar cells), hereditary optic neuropathies (retinal ganglion cells) but for the majority of cases the cause is mutation in genes expressed in the photoreceptor or retinal pigment epithelial (RPE) cells. Mutations in over 200 genes have been identified that cause IRDs (http://www.sph.uth.tmc.edu/RetNet/) with a range of inheritance patterns exhibited. The most common IRD is retinitis pigmentosa, for which at least 30 genes have been associated. Around 10% of retinal disease cases are the result of early onset retinal dystrophy. For example, Leber congenital amaurosis (LCA, MIM204000) is a common cause of blindness in childhood (10%). It is the most severe inherited retinal dystrophy, responsible for blindness or profound visual deficiency at birth or in the first months of life. In the following months, the disease will either present as a dramatically severe and stationary cone-rod disease with extremely poor visual acuity (VA≤light perception; type I) or a progressive, yet severe, rod-cone dystrophy with measurable visual acuity over the first decade of life (20/200≤VA≤60/200; type II). Hitherto, alterations of 18 genes with highly variable patterns of tissular distribution and functions have been reported in LCA (Kaplan, J. Ophthalmic Genet. 29, 92-8 (2008); den Hollander, A I et al. Prog Retin Eye Res. 27, 391-419 (2008); Perrault, I et al. Nat Genet (2012)). In Western countries, mutations affecting the centrosomal protein 290 (CEP290) are the main cause of the disease (20%) (den Hollander. A I et al. Am J Hum Genet. 79, 556-61 (2006); Perrault, I et al. Hum Mutat. 28, 416 (2007).). Among them, the c.2991+1655 A>G mutation accounts for over 10% of all LCA cases, making this change an important target for therapy. The mutation is located deep in intron 26 and creates a strong donor splice site downstream of a strong cryptic acceptor splice site. As a result, in addition to wild-type messengers, mutant mRNAs are transcribed from the mutant allele. The mutant mRNAs include an additional exon encoding a stop codon.

Considering the potential of exon skipping as a mean to bypass protein truncations resulting from a mutation, antisense oligonucleotide-mediated exon skipping strategy is currently investigated to correct the aberrant splicing in retina of a subject suffering from a retinal disease. This approach appears particularly promising. Indeed: 1) spectacular results were recently reported in patients with Duchenne Muscular dystrophy who received muscular injections of therapeutic antisense oligonucleotides to skip DMD mutant exons (Heemskerk et al., Ann N Y Acad Sci. 2009), 2) the wild-type protein is expressed from the mutant allele (in small quantities) preventing the risk of immune response after exon skipping. Thus it was recently reported the proof-of-concept of antisense oligonucleotides-mediated exon skipping to correct the common deep intronic CEP290 mutation in LCA patient fibroblasts which recovered control wild-type mRNA and protein abundance and ciliation ability (Gerard et al., 2012 MTNA), 3) the eye is a small, confined and immune privileged organ and thus low doses of AONs are required to obtain a therapeutic effect, thus reducing the risk of dissemination of the product into the general circulation, 4) In murides, rabbits and primates intravitreal injections of stabilized antisense oligonucleotides allow a wide distribution through-out all retinal layers with sustained concentrations for several weeks (Rakoczy et al., 1996; Leeds et al., 1998; Shen et al., 2002), 5) Safety and efficacy of repeated intravitreal injections of the FDA approved AON Vitravene® to interfere with cytomegalovirus mRNA in immunocompromized patients affected with retinitis and, 6) AONs can alternatively be delivered using unique intravitreal injections, or subretinal injections whose midterm efficacy and safety have been demonstrated in RPE65 clinical trials (Bainbridge et al., N Engl J Med. 2008; Hauswirth et al., Hum Gene Ther., 2008, Maguire et al., N Engl J Med., 2008; Maguire et al., Lancet., 2009).

The major drawbacks of adenoviral delivery of AONs in outer retinal cells (photoreceptors and RPE) are 1) technical prejudice: it is only possible to reach transduction of outer retinal cells through a subretinal injection that causes retinal detachment with possible serious adverse effects, 2) technical limitations: limited retinal detachment and thus limited distribution of adenoviral particules; need to adapt the AAV serotype that transduce efficiently the target retinal cells and (Dalkara et al., Gene Ther., 2012) 3) medical uncertainties: absence of clearance of the adenoviral particule in the retina; possible ectopic expression of a retinal specific protein (Stieger et al., Mol Ther., 2008) which could lead to the rise of antibodies that could insult the retina (e.g. cancer associated retinopathy due to ectopic expression of recoverin by the tumor, Matsubara et al., Br J Cancer., 1996).

SUMMARY OF THE INVENTION

The inventors now overcome the prejudice and limitations by surprisingly demonstrating that it is possible to perform antisense oligonucleotide mediated exon skipping in retina with intravitreal injections of the antisense oligonucleotide. The results, although preliminary provide first and highly convincing evidence for the proof of concept of the use of this strategy to modify the splicing of pre-mRNA in the nucleus of all retina cell layers, including photoreceptors cells. Accordingly, the present invention is defined by the claims.

DETAILED DESCRIPTION OF THE INVENTION

Definitions

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is comprised exclusively of exons. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" refers to the modification of a pre-mRNA following transcription, in which introns are removed and exons are joined. Splicing occurs in a series of reactions that are catalyzed by a large RNA-protein complex composed of five small nuclear ribonucleo-proteins (snRNPs) referred to as a spliceosome and more than 100 other factors (Will et Lührmann, *Curr Opin Cell Biol.* 2001). Within an intron, a 3' splice site, a 5' splice site, and a branch site are required for splicing. The splicing co-factors (eg serine-arginine proteins, SR; heterogeneous nuclear ribonucleoproteins, hnRNP) bind to their recognition motif at the pre-mRNA (intronic and exonic sequences) to manage the recruitment of UsnRNPs. The RNA components of snRNPs interact with the intron and may be involved in catalysis. Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is also regulated by intronic and exonic regulatory sequence i.e. intronic sequence silencer (ISS), intronic sequence enhancer (ISE), exonic sequence silencer (ESS), exonic sequence enhancer (ESE), and terminal stem loop (TSL) sequences. As used herein, the terms "intronic sequence silencer (ISS)", "intronic sequence enhancer (ISE)", "exonic sequence silencer (ESS)", "exonic sequence enhancer (ESE)", and "terminal stem loop (TSL)" refer to sequence elements within introns or exons that control alternative splicing by the binding of trans-acting protein factors within a pre-mRNA thereby resulting in differential use of splice sites. Typically, intronic silencer sequences are between 8 and 16 nucleotides and are less conserved than the splice sites at exon-intron junctions. Terminal stem loop sequences are typically between 12 and 24 nucleotides and form a secondary loop structure due to the complementarity, and hence binding, within the 12-24 nucleotide sequence. The existence of other regulation sequences have also been showed and include *Exonic Splicing Enhancer* (ESE) and *Exonic Splicing Silencer* (ESS) (Liu et al, *Genes Dev.,* 1998; Cartegni et Krainer, *Nat Genet,* 2002; Wang et Burge, *RNA,* 2008).

As used herein, the term "exon skipping" refers to the modification of pre-mRNA splicing by the targeting of splice donor and/or acceptor and branch sites within a pre-mRNA with one or more complementary antisense oligonucleotide(s) (AONs). By blocking access of a spliceosome to one or more splice donor, acceptor or branch site, an AON can prevent a splicing reaction thereby causing the exclusion of one or more exons from a fully-processed mRNA. Exon skipping is achieved in the nucleus during the maturation process of pre-mRNAs. It includes the masking of key sequences involved in the splicing of targeted exons by using antisense oligonucleotides (AON) that are complementary to splice donor/acceptor, branch-point sequences and/or by overlapping ESE (in exon)/ISE (in intron) within a pre-mRNA.

As used herein, the term "antisense oligonucleotide (AON)" refers to an oligonucleotide that is capable of interacting with and/or hybridizing to a pre-mRNA or an mRNA having a complementary nucleotide sequence thereby modifying gene expression. Typically, the antisense oligonucleotide is complementary to the nucleic acid sequence that is necessary for preventing splicing of the targeted exon including cryptic exon, supplementary exon, pseudo-exon or intron sequence retained after splicing.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the AON of the present disclosure, the binding free energy for a AON with its complementary sequence is sufficient to allow the relevant function of the AON to proceed and there is a sufficient degree of complementarity to avoid non-specific binding of the AON to non-target sequences under conditions in which specific binding is desired, i.e., under physiological conditions in the case of in vivo therapeutic treatment. Determination of binding free energies for nucleic acid molecules is well known in the art (see e.g., Turner et ah, CSH Symp. Quant. Biol. 1/7:123-133 (1987); Frier et al, Proc. Nat. Acad. Sci. USA 83:9373-77 (1986); and Turner et al, J. Am. Chem. Soc. 109:3783-3785 (1987)). Thus, "complementary" (or "specifically hybridizable") are terms that indicate a sufficient degree of complementarity or precise pairing such that stable and specific binding occurs between an AON and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary.

Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

In the context of the invention, the term "treating" or "treatment", as used herein, means reversing, alleviating, inhibiting the progress of, or preventing the disorder or condition to which such term applies, or one or more symptoms of such disorder or condition (e.g., retinal degenerative or stationary diseases).

According to the invention, the term "subject" or "patient in need thereof", is intended for a human or non-human mammal affected or likely to be affected with a retinal disease.

METHODS OF THE INVENTION

The present invention relates to a method for performing antisense oligonucleotide-mediated exon skipping in a retina cell of a subject in need thereof comprising the step of injecting into the vitreous of the subject an amount of the antisense oligonucleotide.

Typically the retina cells for which the method of the invention may be carried out include but are not limited to bipolar cells, Miller cells, photoreceptors cells (cone and rod), or retinal pigment eptithelial (RPE) cells, ganglion cells, horizontal cells, amacrine cells.

The method of the invention is particularly suitable for the treatment of a retinal disease. Indeed the method of the invention is particularly suitable for a mutated gene causing a retinal disease. For example, the retinal diseases include but are not limited to the diseases reported in Table A. In one embodiment, the retinal disease is a retinal stationary disease or a retinal degenerative disease.

Retinal degenerative disease include but are not limited to Retinitis Pigmentosa, age-related macular degeneration, Bardet-Biedel syndrome, Bassen-Kornzweig syndrome, Best disease, choroidema, gyrate atrophy, Leber congenital amaurosis, Refsun syndrome, Stargardt disease, Usher syndrome or hereditary optic neuropathies (HON). Stationary retinal disease include but are not limited to congenital stationary night blindness (CSNB), dyschromatopsia or achromatopsia.

In one embodiment, the retinal disease is Leber congenital amaurosis associated with c.2991+1655 A>G mutation.

The AON's used in the practice of the invention may be of any suitable type, e.g. oligodeoxyribonucleotides, oligoribonucleotides, morpholinos, tricyclo-DNA-antisense oligonucleotides, U7- or U1-mediated AONs or conjugate products thereof such as peptide-conjugated or nanoparticle-complexed AONs. AONs employed in the practice of the invention are generally from about 10 to about 50 nucleotides in length, and may be for example, about 10 or fewer, or about 15, or about 20 or about 30 nucleotides or more in length. The optimal length of the AON's for a targeted complementary sequence is generally in the range of from about 15 to about 30 nucleotides long depending on the chemical backbone used and on the target sequence. Typically, morpholino-AONs are about 25 nucleotides long, 2'PMO-AONs are about 20 nucleotides long, and tricyclo-AONs are about 15 nucleotides long.

For use in the instant invention, the AONs of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, AON's can be produced on a large scale in plasmids (sec Sambrook, et al., 1989). AON's can be prepared from existing nucleic acid sequences using known techniques, such as those employing restriction enzymes, exonucleases or endonucleases. AON's prepared in this manner may be referred to as isolated nucleic acids.

For use in vivo, the AONs may be or are stabilized. A "stabilized" AON refers to an AON that is relatively resistant to in vivo degradation (e.g. via an exo- or endonuclease). Stabilization can be a function of length or secondary structure. Alternatively, AON stabilization can be accomplished via phosphate backbone modifications. Preferred stabilized AON's of the instant invention have a modified backbone, e.g. have phosphorothioate linkages to provide maximal activity and protect the AON from degradation by intracellular exo- and endo-nucleases. Other possible stabilizing modifications include phosphodiester modifications, combinations of phosphodiester and phosphorothioatc modifications, methylphosphonate, methylphosphorothioate, phosphorodithioate, p-ethoxy, and combinations thereof. Chemically stabilized, modified versions of the AON's also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

In a particular embodiment, the antisense oligonucleotides of the invention may be 2'-O-Me RNA/ENA chimera oligonucleotides (Takagi M, Yagi M, Ishibashi K, Takeshima Y, Surono A, Matsuo M, Koizumi M. Design of 2'-O-Me RNA/ENA chimera oligonucleotides to induce exon skipping in dystrophin pre-mRNA. Nucleic Acids Symp Ser (Oxf). 2004; (48):297-8).

Other forms of AONs that may be used to this effect are AON sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

In a particular embodiment, the AONs may also be coupled to a peptide (e.g. penetrating peptide) to facilitate the cellular uptake (Fletcher et al. Mol Ther 2007).

In another particular embodiment, the antisense oligonucleotides of the invention are 2'-O-methyl-phosphorothioate oligonucleotides.

One skilled in the art may be easily identified the antisense oligonucleotide that may be suitable for carrying out the method of the invention. Many methods and told have been indeed developed for designing an AON that is able to target the exon of interest. For example, mfold software and ESEfinder program (for details see: Gerard et al., 2012) may used. Furthermore many suitable antisense oligonucleotides have been also described in the prior art. For example, the antisense oligonucleotides described in WO2012168435 may be suitable for targeting c,2991+1655 A>G.

One essential feature of the invention it that the antisense oligonucleotide is not delivered in association with a viral vector. Accordingly, the antisense oligonucleotide is injected alone (i.e. "naked") in the vitreous of the patient and use of viral vectors is thus excluded from the scope of the invention. Typically, viral vectors include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. In particular, use of adenoviruses and adeno-associated (AAV) viruses, which are DNA viruses that have already been approved for human use in gene therapy are excluded from the scope of the invention.

Typically, the antisense oligonucleotide is injected in the vitreous of the patient in a therapeutically effective amount. As used herein, the term "therapeutically effective amount" means an amount of AON that is sufficient, in the subject (e.g., human) to which it is administered, to treat or prevent the retinal disease. One skilled in the art will recognize that the amount of an AON to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.).

Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the AONs of the invention will likely be injected on multiple occasions, that may be, depending on the results obtained, several days apart, several weeks apart, or several months apart, or even several years apart. Indeed, chronically intravitreal injections of the antisense oligonucleotide may be needed to reach a therapeutic effect in a long term manner. This is especially true where the treatment of Leber congenital amaurosis is concerned since the disease is not cured by this treatment, i.e. the gene that encodes the protein will still be defective and the encoded protein will still possess an unwanted, destabilizing feature such as an exposed proteolytic recognition site, unless the AONs of the invention are administered.

The present invention also provides a pharmaceutical composition containing an antisense oligonucleotide of the invention that is compatible for intravitreal injection. Typically, the pharmaceutical compositions of the present invention include a pharmaceutically or physiologically acceptable carrier such as saline, sodium phosphate, etc., although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc.

The invention will be further illustrated by the following figures and examples. However, these examples and figures should not be interpreted in any way as limiting the scope of the present invention.

FIGURES

FIG. 1: Schematic representation of skipping of exon 23 (A) and exon 36 (B) induced by 2'-OMePS oligonucleotides on the wild-type Cep290pre-mRNA in mouse. For each exon mentioned, two AONs were designed to target the donor splice site and an exonic splice enhancer (ESE) sequence. The m23D(+11-18) 5'-GUUUU-CAAAAUAUAAAUACCUUAGGUAUUC-3' (SEQ ID NO:28), m23ESE(+50+70) 5'-GAUGACGAAUCA-CUGCAAAC-3' (SEQ ID NO:29), m36D(+8-16) 5'-GUU-CUCAGAAUCUUACCUGAGCUG-3' (SEQ ID NO:30) and m36ESE(+23+44) 5'-CAUGAAGGUCUUCCU-CAUGC-3' (SEQ ID NO:31) AONs were called m23D, m23ESE, m36D and m36ESE, respectively thereafter. The m23ESEsense is a sense version of m23ESE(+50+70) 5'-GUUUGCAGUGAUUCGUCAUC-3' (SEQ ID NO:32) and used as control.

Figure 2A:
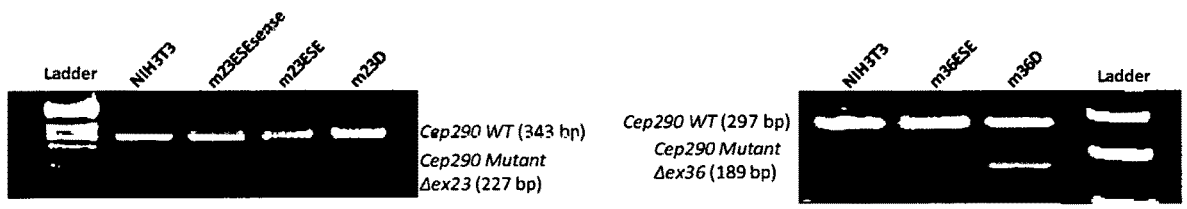
Figure 2B:
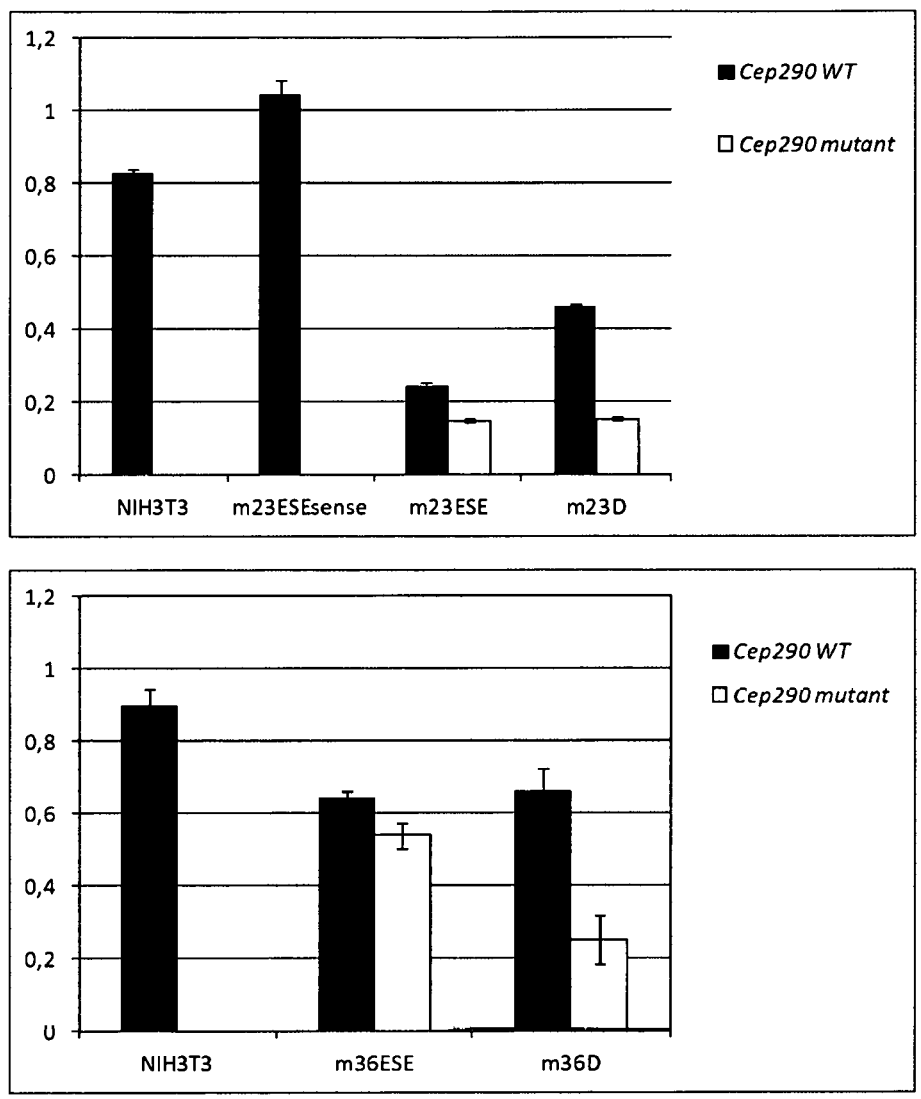
Figure 2C:
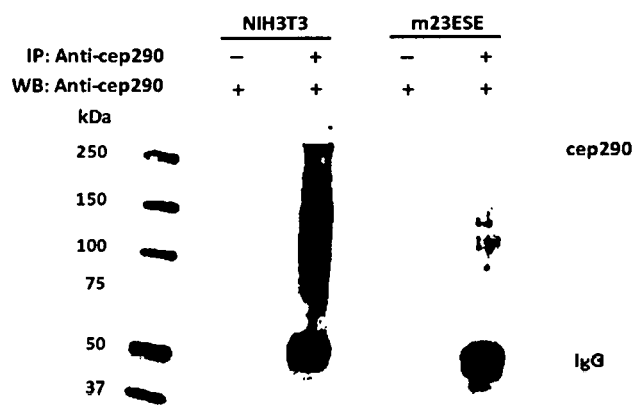

FIG. 2: Effect of AON-mediated skipping of the Cep290 exon 23 and 36 on the wild-type messenger RNA (mRNA). (A) Presentation of PCR analysis of mRNA extracted from non-treated NIH3T3 and after 24 hours of cell transfection with 150 nM of m23ESE and m23D AON as well as m23ESEsense ON control [left]; and cells transfected with 150 nM of m36ESE and m36D [right], respectively. Bands were analyzed by sequencing to ensure of specific skipping of exon 23 and 36 after treatment. (B) RT-qPCR analysis showing the relative expression of wild-type (WT) and mutant (Δex23 [left]; Δex36 [right]) transcripts of Cep290 gene in transfected cells compared to non-treated NIH3T3, under the same conditions as those mentioned above. The error bars represent the standard deviation of the mean derived from three independent experiments. Results were normalized using Gusb and Ppia genes as reference. (C) Western blot (WB) analysis using a rabbit polyclonal antibody raised against the C-terminal residues of cep290 (+). Because classical western blot analysis of 150 µg of total protein from non-treated NIH3T3 cells or 24 hours post-transfection with m23ESE AON gave not suitable results (−), 800 µg of total protein for the both conditions were subjected to immune-precipitation (IP) (+). Similar results were obtained from at least three independent experiments.

FIG. 3: Kinetic of AON following a single injection into the vitreous of C57BL/6J mice. (A) RT-PCR analysis of Cep290 mRNA extracted from non-treated and retinas injected with 1 µl of saline solution containing 10 nmol of m23D AON that were taken 2, 6 or 10 days post-injection, respectively. The upper band represents the wild-type Cep290 splice product, whereas the lower band represents the mutant Δex23 Cep290 splice product. Bands were analyzed by sequencing to ensure of specific skipping of exon 23 after treatment. (B) Series of 1, 2 or 3 C57BL/6J mice were non-treated or injected, as described above. RT-qPCR analysis showing the relative expression of wild-type (WT) and mutant (Δex23) transcripts of Cep290 gene in control and injected retinas. Results were normalized using Tbp and Hprt1 genes as reference.

Figure 4:
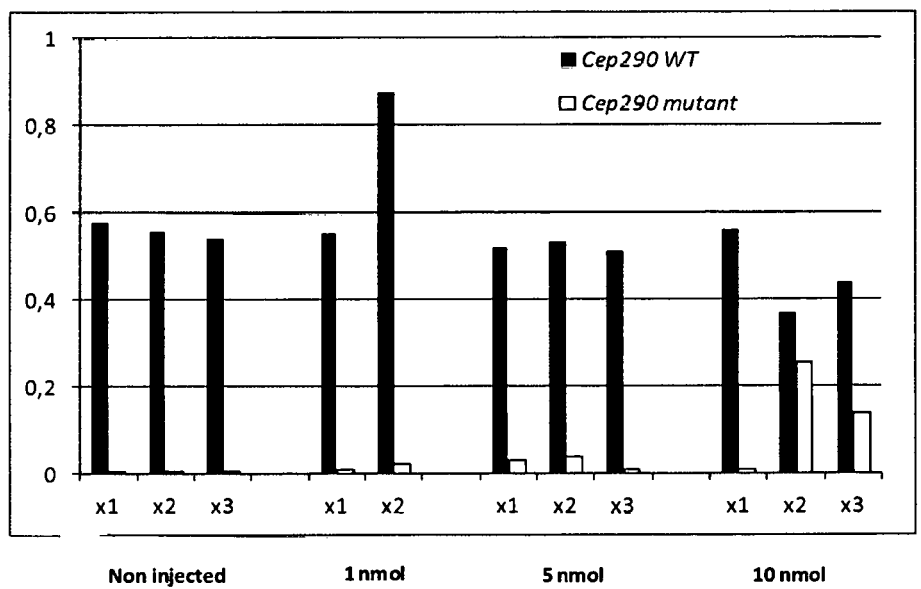

FIG. 4: Dose-dependent effect and distribution of AON two days post-injection. Series of 2 or 3 C57BL/6J mice were injected with 1 µl of saline solution containing 1 nmol, 5 nmol or 10 nmol of fluorescently labelled (6-FAM) m23D AON, into the vitreous. RT-qPCR analysis showing the relative expression of wild-type (WT) and mutant (Δex23) transcripts of Cep290 gene in control and injected retinas. Results were normalized using Tbp and Hprt1 genes as reference.

Figure 5:
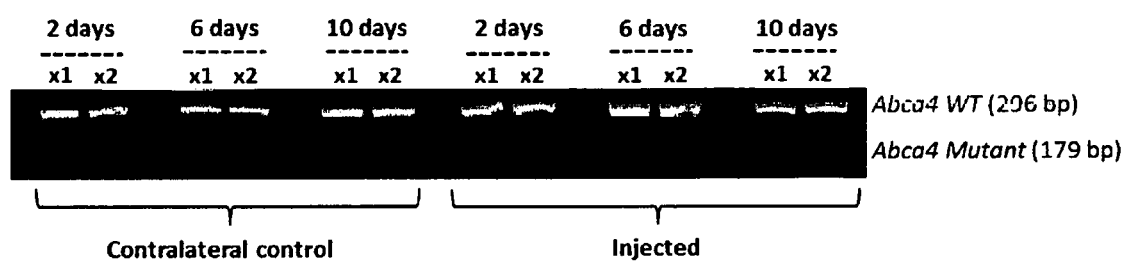

FIG. 5: Exon skipping in photoreceptors. Presentation of PCR analysis of mRNA extracted from retina of two different mice, 2, 6 and 10 days post-injection of 10 nmol of AON compared to retina non-injected contralateral. Bands were analyzed by sequencing to ensure of specific effect on the Abca4 transcript after treatment.

EXAMPLES

Here, we describe a new method to treat patients suffering from a retinal disease due to a mutation that modifies the splicing and/or creates a premature termination, in a gene important to the functioning and/or the survival of a given retinal cell type. The method consists in skipping a nucleotidic sequence by intravitreal injections of a stabilized antisense oligonucleotideto reach the whole retinal surface and to target the pre-mRNA from a gene which mutation cause inherited retinal diseases.

To demonstrate the feasibility of this novel therapeutic strategy, we have chosen to target mouseubiquitously expressed genes, and genes harboring a retinal-cell specific pattern of expression.

CEP290: This gene spans 54 exons and is transcribedas a 7.9 kb mRNA that encodes a centrosomal protein of 290 kDa. In the retina, it is expressed in at least the ganglion cell layer, the inner nuclear layer and the photoreceptors cell layer (Baye et al., 2011). With respect to photoreceptor cells, the protein plays a crucial role in maintaining structure and function of the connecting cilium that allows molecular trafficking between the inner and outer segments. CEP290 is the most frequently involved in Leber's congenital amaurosis, which is the earliest and the most severe retinal dystrophy (Perrault et al., 2007).

ABCA4: This gene consists in 50 exons and is transcribed into a 7.3 kb messenger of encoding a protein having a molecular mass of 256 kDa. ABCA4 expression is confined to the photoreceptor cells (rods and cones). Stargardt disease, the most common macular dystrophy, is caused by mutations in the gene encoding ABCA4, a photoreceptor ATP binding cassette (ABC) transporter. The protein intervenes as a flippase that facilitates the removal of potentially toxic retinal compounds from photoreceptors following photoexcitation (Molday et al., 2004).

TMEM126A: This gene consistingin 5 exons is transcribed into a 0.7 kb messenger encoding a transmembrane mitochondrial protein of 21.5 kDa. In retina, TMEM126A has a strong expression in the ganglion cell layer, the optic nerve head, the inner nuclear layer, and the outer plexiform layer, which are particularly enriched in mitochondria. To date, the function of TMEM126A is unknown but its alteration is responsible for autosomal recessive optic neuropathy characterized by the degeneration of optic nerve fibers (Hanein et al., 2013).

GRM6: The glutamate receptor metabotropic 6 gene contains 10 exons and is transcribed into a 6 kb messenger encoding a protein having a molecular weight expected of 95.5 kDa. The localization of GRM6 is limited to the postsynaptic ending of bipolar cells. This glutamate receptor is involved in signal transmission from photoreceptors to adjacent bipolar cells, the disruption of which lead to congenital stationary night blindness (Maddox et al., 2008).

Example 1: Splice Modulation of Cep290 mRNA

Materials and Methods

Identification of target sequences to Cep290 exon 23 and exon 36 skipping. Bioinformatics analyses to find targetable sequences within exon 23 and exon 36 of the Cep290 pre-mRNA and their surrounding intronic sequences (splice sites), were realized using http://mfold.rna.albany.edu/and http://rulai.cshl.edu/cgi-bin/tools/ESE3/esefinder.cgi.

Murine fibroblast cultures. NIH-3T3 cells (mouse fibroblast cell line) were obtained from the American Type Culture Collection (Rockville, Md.). These cells were cultured in a standard medium consisting of DMEM (Invitrogen) containing 10% FCS, 50 U/ml penicillin and 50 mg/ml streptomycin (Invitrogen). Only cell cultures with a lower passage to 15 were used in our studies.

AONs and transfection. Antisense oligonucleotides specific to donor splice sites and ESE around the two exons were identified by ESEfinder 3.0 program (Cartegni and Krainer, 2003). The corresponding selected sequences are represented in FIG. 1. All AONs were synthetized by Sigma-Aldrich (St Quentin Fallavier, France) and contain 2'-O-methyl RNA and full-length phosphorothioate backbones. NIH-3T3 cells at 80% confluence were transfected in DMEM using Lipofectamine2000 (Invitrogen) according to the manufacturer's instruction. Each 2'-OMePS AON was transfected at 150 nmol/l in at least three separate experiments. A sense version of each ESE AON was used as control to assess the specificity of AONs (FIG. 1). After 4 hours of incubation at 37° C., the transfection medium was replaced by fresh culture medium.

Transfection efficiency. NIH-3T3 cells were seeded on glass coverslips in 12-well plates, 24 hours before transfection. Antisense m23D(xx), m23ESE(xx), m36D(xx) and sense m23ESEsense(xx) oligonucleotides carrying a 5'-end fluorescein group were obtained from Sigma Aldrich. Fibroblasts were transfected as described previously. Untreated fibroblasts were processed in the same conditions. After 4 h of incubation, cells were fixed with PFA 4% (15 minutes at room temperature) and washed twice in PBS. A mounting media containing 4',6-diamidino-2-phenylindole (DAPI) (ProLong Gold antifade reagent with DAPI; Invitrogen) was used to label nuclei. Immunofluorescence images were obtained using a ZEISS LSM700 confocal microscope (Carl Zeiss, Germany). The final images were generated using ImageJ (National Institutes of Health, Bethesda, Mass.). Percentages of fluorescent cells were calculated (over 90% of all cells were labelled) from three independent experiments for each oligonucleotide transfection (n>100 counted cells for each transfection).

AON intravitreal injection of experimental animals. All animal experiments adhered to the Association for Research in Vision and Ophthalmology statement for the use of animals in ophthalmic and vision research. Eight-week-old C57BL/6J mice were used for these experiments. The animals were anesthetized by intramuscular injection of mixture solution of ketamine (100 mg/kg) and xylazine (10 mg/kg). The pupils were dilated with 10% phenylephrine and 0.5% tropicamide. A 30 gauge needle was used to make an initial puncture of the sclera. Through this hole a 33 gauge needle attached to a 5 µl Hamilton syringe was passed into the vitreous cavity. The advancement of the needle was directly observed under a binocular when the needle tip lay in the vitreous cavity. The left eyes were injected with 1 µl of saline solution (NaCl 9 g/l, pH=8.7) containing 1, 5 or 10 nmol of 6-FAM oligonucleotides (m23D), respectively, into the vitreous. The needle was kept in the vitreous cavity for about 20 seconds then withdrawn gently and antibiotic ointment was applied to prevent infection. The right eyes were non-injected and used as contralateral controls. The injected and contralateral eyes were enucleated at 2, 6 or 10 days after injection and processed for further analysis. The sampled eyes were either immersed in PFA 4% to be cut and mounted onto glass slides and examined by confocal microscopy (ZEISS LSM700) after nuclei labeled using DAPI (ProLong Gold antifade reagent with DAPI; Invitrogen); or the retinas were extracted to recover ARN as described below. Between 2 and 5 animals were used for each experimental setup.

RNA extraction and cDNA synthesis. Twenty-four hours after transfection, the transfected and untreated cells were processed. Similarly, RNA from retinas at 2, 6 and 10 days post-injection for both injected and non-injected eyes were obtained as below. Total RNA was extracted using the RNeasy Mini Kit (Qiagen, Courtaboeuf, France) according to manufacturer's protocol. All samples were DNase treated by the RNase-free DNase set (Qiagen, Courtaboeuf, France). Concentration and purity of total RNA was assessed using the Nanodrop-1000 spectrophotometer (Fisher Scientific, Illkirch, France) before storage at −80° C. First-stranded cDNA synthesis was performed from 500 ng of total RNA extracted using Verso cDNA kit (Thermo Fisher Scientific) with random hexamer:anchored oligo(dT) primers at a 3:1 (vol:vol) ratio according to the manufacturer's instructions. A non-RT reaction (without enzyme) for one sample was prepared to serve as control in RT-qPCR experiments.

Reverse transcription PCR (RT-PCR). To assess the efficiency of AON-mediated exon skipping, cDNAs (5 µl) were amplified in 50 µl of 1× Phusion HF buffer containing 5 mM dNTPs (Fischer Scientific, Illkirch, France), 0.02 units of Phusion High-Fidelity DNA polymerase (Fischer Scientific, Illkirch, France) and 10 µM of each primer Cep290(ex22) forward, 5'-gaccaccttgagaaggaaac-3' (SEQ ID NO:1) and Cep290(ex24) reverse, 5'-catcctgctcagcttgatc-3' (SEQ ID NO:2) or Cep290(ex35) forward, 5'-cccaccaaactattgccaac-3' (SEQ ID NO:3) and Cep290(ex37) reverse, 5'-gagagtcatcttgttctgctac-3' (SEQ ID NO:4). PCRs were carried out on a 2720 Thermal Cycler (Applied Biosystems, Courtaboeuf, France) under the following conditions: initial denaturation at 98° C. for 5 min, followed by 30 cycles of 10 sec-denaturation at 98° C., 30 sec-annealing at 60° C. and 30 sec-extension at 72° C. The PCR products were separated (20 µl) by electrophoresis in a 3% agarose gel stained with ethidium bromide and visualized under UV lights. No template (NTC) reactions were used as negative control. The final confirmation of identity of these products was carried out by Sanger sequencing to establish that the correct and expected exon junctions have been maintained.

Real-time quantitative PCR (RT-qPCR). To measure the level of expression of Cep290 mRNAs, the wild-type and mutant transcripts were amplified as 102 and 75 bp fragments (exon 23 skipping), respectively; or the wild-type and mutant transcripts were amplified as 100 and 62 bp fragments (exon 36 skipping), respectively. The mouse TATA boxbinding protein mRNA (Tbp), the mouse β-2-microglobulin mRNA (B2m), the mouse β-glucuronidase mRNA (Gusb), the mouse hypoxanthine phosphoribosyltransferase 1 mRNA (Hprt1), and the mouse peptidylprolyl isomerase A mRNA (Ppia) were used for normalization. The mouse albumin gene (Alb) was used to control the non-contamination of cDNAs by genomic DNA. Primers were designed using the Oligo Primer Analysis Software v. 7 available at http://www.oligo.net. The specificity of primer pairs to PCR template sequences was checked against the NCBI database using the Primer-BLAST software (ncbi.nlm.nih.gov/tools/primer-blast). Primer sequences were as follows: Cep290ex23 wt forward, 5'-tgactgctaagtacagggacatct tg-3' (SEQ ID NO:5); Cep290ex23 wt reverse, 5'-aggagatgttttcacactccaggt-3' (SEQ ID NO:6); Cep290ex23mt forward, 5'-ctggccccagttgtaatttgtga-3' (SEQ ID NO:7); Cep290ex23mt reverse, 5'-ctgttcccaggcttgttcaatagt-3' (SEQ ID NO:8); Cep290ex36 wt forward, 5'-tgactgctaagtacaggga-catct tg-3' (SEQ ID NO:9); Cep290ex36 wt reverse, 5'-aggagatgttttcacactccaggt-3' (SEQ ID NO:10); Cep290ex36mt forward, 5'-ctggccccagttgtaatttgtga-3' (SEQ ID NO:11); Cep290ex36mt reverse, 5'-ctgttcccaggcttgttcaatagt-3' (SEQ ID NO:12); reference genes Tbp forward, 5'-tgacctaaagac-cattgcacttcgt-3' (SEQ ID NO:13); Tbp reverse, 5'-ctgcagcaaatcgcttggga-3' (SEQ ID NO:14); B2m forward, 5'-cctgtatgctatccagaaaaccct-3' (SEQ ID NO:15); B2m reverse 5'-cgtagcagttcagtatgttcggctt-3' (SEQ ID NO:16); Gusb forward, 5'-ctgcggttgtgatgtggtctgt-3' (SEQ ID NO:17); Gusb reverse, 5'-tgtgggtgatcagcgtcttaaagt-3' (SEQ ID NO:18); Hprt1 forward, 5'-gttggatacaggccagacttgtt-3' (SEQ ID NO:19); Hprt1 reverse, 5'-aaacgtgattcaaatccctgaagta-3' (SEQ ID NO:20); Ppia forward, 5'-ccaaacacaaacggttcccagt-3' (SEQ ID NO:21); Ppia reverse, 5'-gcttgccatccagccattca-3' (SEQ ID NO:22); Alb forward 5'-gggacagtgagtacccaga-catcta-3' (SEQ ID NO:23); Alb reverse 5'-ccagacttggtgttg-gatgctt-3' (SEQ ID NO:24). cDNAs (5 µl of a 1:25 dilution in nuclease-free water) were subjected to real-time PCR amplification in a buffer (20 µl) containing SYBR GREEN PCR Master Mix (Applied Biosystems, Courtaboeuf, France) and 300 nmol/l of forward and reverse primers, on a MasterCycler epgradients Realplex$^2$ (Eppendorf, Germany) under the following conditions: Taq polymerase activation and initial denaturation at 95° C. for 15 minutes, followed by 50 cycles for 15 seconds at 95° C., and 1 minute at 62° C. The specificity of amplification products was determined from melting curve analysis performed at the end of each run using a cycle at 95° C. for 15 seconds, 60° C. for 15 seconds, and 95° C. for 15 seconds. Data were analyzed using the Realplex software (Eppendorf, Germany). For each cDNA sample, the mean of quantification cycle (Cq) values was calculated from triplicates (SD<0.5 Cq). Cep290 expression levels were normalized to the "normalization factor" obtained from the geNorm software for Microsoft Excel which uses the most stable reference genes and amplification efficiency estimates calculated for each primer pair using fourfold serial dilution curves (1:5, 1:25, 1:125, 1:625). No reverse transcriptase (non-RT), no template control (NTC) reactions, and non-contamination of cDNAs by genomic DNA (ALBh) were used as negative controls in each run (Cq values NTC=undetermined, non-RT>38 and ALBh>38). The quantitative data are the means±SD of three independent experiments and these are presented as ratio among values for individual mRNAs.

Protein extraction, immunoprecipitation and Western blot analysis. Cells were harvested 24 hours after transfection and lysed in RIPA buffer (Sigma) containing complete protease inhibitor cocktail (1%; Sigma) on ice for 1 hour with repeated mixing. Lysis was accomplished by 15 seconds of sonication on ice (Bioblock Scientific VibraCell 72434) and the lysates were centrifuged (13,000 rpm at 4° C. for 10 minutes). 800 µg of protein extracts were analysed by immunoprecipitation (IP) using µMacs Separation Columns and µMacs Protein G Microbeads (Miltenyi Biotec) with a rabbit polyclonal anti-cep290 (1:100; Novus Biologicals, Littletown, Colo.), according to supplier's recommendations. 150 µg of initial protein extracts (resuspended with LDS sample buffer 1× (Life Technologies, USA) with 10% β-mercaptoéthanol) and immunoprecipitates were heated at 90° C. for 10 min and loaded on a 4-15% Mini-PROTEAN TGX precast polyacrylamide gels (BioRad). After electrophoresis, proteins were transferred to a 0.2 µm PVDF membrane using the Trans-Blot Turbo transfer system (Bio-Rad) which was probed with the following primary antibody: rabbit polyclonal anti-human Cep290 (1:1800; Novus Biologicals, Littletown, Colo.) and secondary antibody: goat anti-rabbit IgG-HRP (1:5,000, Abeam, France). Blots were revealed with the use of SuperSignal® West Dura Extended Duration Substrate (Thermo Scientific, USA) and Chemi-Doc XRS+Imaging System (Bio-Rad, USA). Western blot images were acquired and analyzed with the Image Lab Software 3.0.1 build 18 (Bio-Rad, USA).

Results

Evaluation of the Safety and the Efficacy of Single Intravitreal Injection of Therapeutic AONs Considering that the transgenic mouse line harbouring the human mutant intron 26 (c.2991+1655A>G) is not yet available, we designed AON sequences to skip wild-type mouse exons. We chose to skip exon 23 and exon 36, respectively. The skipping of exon 23 is expected to result in a shift of the reading frame and to the production, if stable, of a truncated protein (FIG. 1A). In contrast, the skipping of exon 36 is expected to preserve the reading frame (FIG. 1B).

Antisense oligonucleotides specific to donor splice sites and ESE around the two exons (m23ESE, m23D, m36ESE, m36D; FIG. 2) were tested in vitro using NIH-3T3 mouse fibroblast line according to our protocol reported in MTNA (Gerard et al., 2012). The potential of AONs to induce skipping was first determined by reverse-transcription PCR (RT-PCR) analysis using mRNA extracted from non-treated and transfected NIH-3T3 cells. Transfection NIH-3T3 cells using 150 nM of AONs resulted in skipping as shown by the apparition of shorter PCR bands which Sanger sequencing demonstrated loss of exon 23 and 36 respectively.

Skipping efficiencies were quantified using real-time quantitative PCR (RT-qPCR) by measuring the level of expression of the wild-type and mutant transcripts in non-transfected versus transfected NIH3T3 fibroblasts. Compared to non-transfected cells or cells transfected with sense ONs, NIH-3T3 cells treated with AONs exhibited significantly decreased wild-type mRNA expression supporting efficient skipping. Accordingly, mutant mRNAs were detected in treated cell lines. The abundance of mutant mRNA lacking exon 23 might be underestimated due to possible non-sense mediated mRNA decay, NMD (frame-shifting skipping with apparition of a premature termination codon). In addition, NIH-3T3 cells were transfected using fluorescently-labeled m23D and m36D antisense and m23ESEsense oligonucleotides to make sure that these results were not due to reduced delivery of the sense oligonucleotide. Similar transfection efficiencies were measured (>90%).

Western blot analyses of immune-precipitated cep290 (pull-down assay) showed that the transfection of cells using the m23ESE AON caused a decrease in ccp290 abundance, giving strong support to the view that the lowering of wild-type transcript levels resulted that of protein amounts.

Altogether, our results demonstrate effectiveness and sequence-dependent ability of identified AONs to induce skipping.

AON-Induced Modification on the Cep290 mRNA in Mouse Photoreceptors

Figure 3A:
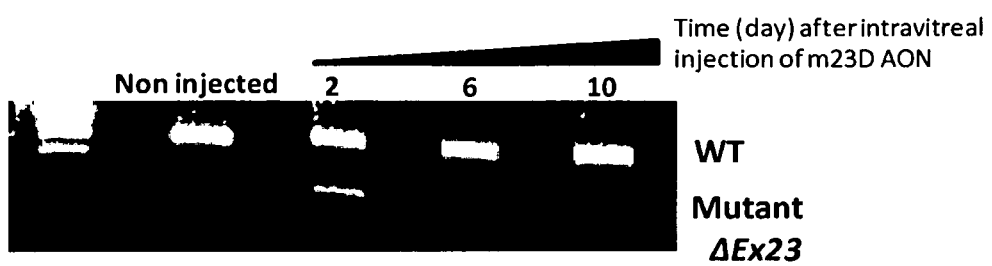

To assess in vivo skipping efficiency following intravitreal injections we used the fluorescently-labeled m23D AON. Ten nmol of AON were injected into the vitreous of the left eye of 8 week-old C57BL/6J mice. The animals were sacrificed at day 2, 6 and 10 post-injection and both injected (left) and non-injected (right) eyes were dissected to isolate neuroretinas. Messenger-RNAs were prepared from treated and untreated retinas. RT-PCRs were performed using primers able to amplify both the wild-type and modified Cep290 transcripts, whereas RT-qPCRs were performed using primers specific to the wild-type mRNA and the mutant transcript lacking exon 23. Agarose gel electrophoresis analysis of RT-PCR products showed that in contrast to non-injected eyes, 2, 6 and 10 day-treated eyes exhibited a lower size product in addition to the wild-type product (FIG. 3A). Sanger sequencing confirmed the identity of both products (wild-type and mutant mRNA lacking exon 23).

Figure 3B:
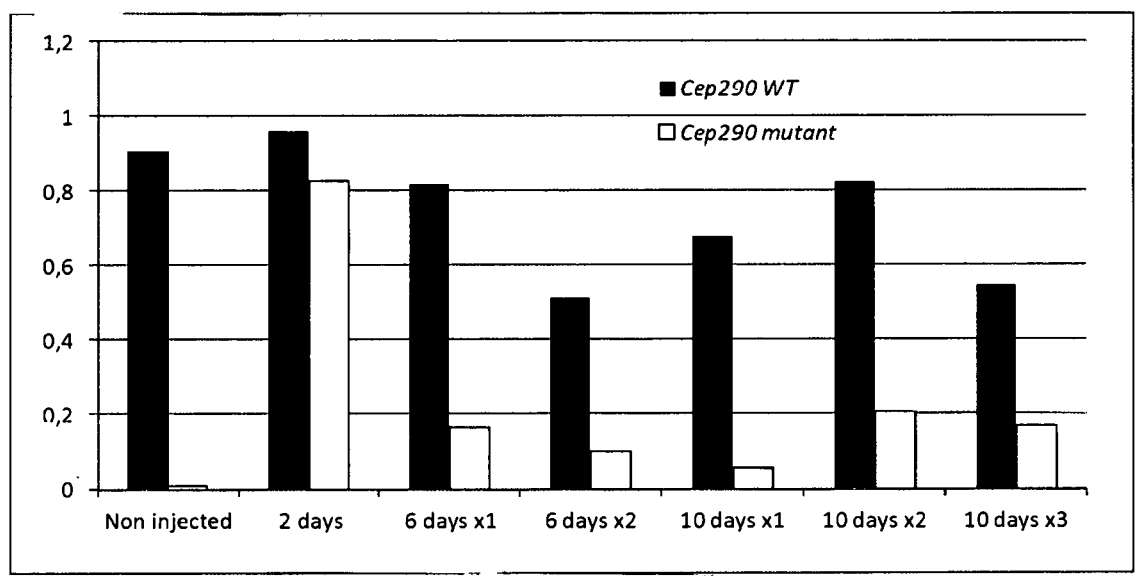

RT-qPCR analysis were consistent with RT-PCR results with decreased expression of wild-type mRNAs in treated eyes compared to non-treated eyes and detectable mutant mRNAs in treated eyes but not in untreated ones (FIG. 3B).

Subsequently, increasing doses of the fluorescently-labeled m23D AON (1, 5, 10 nmol) were injected using the same procedure. Animals were sacrificed at day 2 post-injection. Injected and non-injected eyes were extracted, dissected to recover the retinas or fixed in PFA and included in paraffin for histological analysis. RT-qPCR analysis evidenced a correlation between skipping efficiency and injected dose of AON (FIG. 4). Histological analysis showed a large distribution of AON through-out retinal sections (histological analysis of whole mount retinas are scheduled).

Cep290 is ubiquitously expressed (Papon et al., 2010). In the retina, it is expressed in several cell layers, including the ganglion cell layer, the inner nuclear layer and the photoreceptors cell layer (Baye et al., 2011). But it is in this last cell layer of the retina that the amount of CEP290 protein is the most abundant (Chang et al., 2006). Histological analysis of the distribution of fluorescent AONs in the retina demonstrated the presence of fluorescence in the photoreceptor nuclear layer. However, to confirm that skipping occurred in photoreceptors, we have set up collaboration with M.P. Felder (Institute of Cellular and Integrative Neurosciences, CNRS UPR 3212, University of Strasbourg) to isolate the photoreceptor layer of non-injected and injected eyes using vibratome. This will be performed in the following weeks.

Altogether, our results demonstrate effectiveness of m23ESE AON to induce skipping in retinal cells.

Example 2: Splice Modulation of Abca4 mRNA

Materials and Methods

Identification of target sequences to Abca4 exon 10 skipping. Bioinformatics analyses to find targetable sequences within exon 10 of the Abca4 pre-mRNA and their surrounding intronic sequences (splice sites), were realized using mfold.rna.albany.edu/ and rulai.csh1.edu/cgi-bin/tools/ESE3/esefinder.cgi.

AON. Antisense oligonucleotide specific to ESE sites on the exon 10 was identified by ESEfinder 3.0 program (Cartegni and Krainer, 2003). The corresponding selected sequence: m10ESE (+60+88) 5'-CAAAGAAGTACCAGATCTGGGGCCCTAC-3' (SEQ ID NO: 25). AON was synthetized by Sigma-Aldrich (St Quentin Fallavier, France) and contain 2'-O-methyl RNA and full-length phosphorothioate backbones.

AON intravitreal injection of experimental animals. All animal experiments adhered to the Association for Research in Vision and Ophthalmology statement for the use of animals in ophthalmic and vision research. Eight-week-old C57BL/6J mice were used for these experiments. The animals were anesthetized by intramuscular injection of mixture solution of ketamine (100 mg/kg) and xylazine (10 mg/kg). The pupils were dilated with 10% phenylephrine and 0.5% tropicamide. A 30 gauge needle was used to make an initial puncture of the sclera. Through this hole a 33 gauge needle attached to a 5 µl Hamilton syringe was passed into the vitreous cavity. The advancement of the needle was directly observed under a binocular when the needle tip lay in the vitreous cavity. The left eyes were injected with 1 µl of saline solution (NaCl 9 g/l, pH=8.7) containing 10 nmol of oligonucleotides (m10ESE) into the vitreous. The needle was kept in the vitreous cavity for about 20 seconds then withdrawn gently and antibiotic ointment was applied to prevent infection. The right eyes were non-injected and used as contralateral controls. The injected and contralateral eyes were enucleated at 2, 6 or 10 days after injection and processed for further analysis. The retinas were extracted to recover ARN as described below. Two 2 animals were used for each experimental setup.

RNA extraction and cDNA synthesis. Total RNA from retinas at 2, 6 and 10 days post-injection for both injected and non-injected eyes was extracted using the RNeasy Mini Kit (Qiagen, Courtaboeuf, France) according to manufacturer's protocol. All samples were DNase treated by the RNase-free DNase set (Qiagen, Courtaboeuf, France). Concentration and purity of total RNA was assessed using the Nanodrop-1000 spectrophotometer (Fisher Scientific, Illkirch, France) before storage at −80° C. First-stranded cDNA synthesis was performed from 500 ng of total RNA extracted using Verso cDNA kit (Thermo Fisher Scientific) with random hexamer:anchored oligo(dT) primers at a 3:1 (vol:vol) ratio according to the manufacturer's instructions.

Reverse transcription PCR (RT-PCR). To assess the efficiency of AON-mediated exon skipping, cDNAs (5 µl) were amplified in 50 µl of 1× Phusion HF buffer containing 5 mM dNTPs (Fischer Scientific, Illkirch, France), 0.02 units of Phusion High-Fidelity DNA polymerase (Fischer Scientific, Illkirch, France) and 10 µM of each primer Abca4(ex9) forward, 5'-tgatccagagcctggagtcaa-3' (SEQ ID NO:26) and Abca4(ex11) reverse, 5'-ttcttctccgagctgcctatt-3' (SEQ ID NO:27). PCRs were carried out on a 2720 Thermal Cycler (Applied Biosystems, Courtaboeuf, France) under the following conditions: initial denaturation at 98° C. for 5 min, followed by 30 cycles of 10 sec-denaturation at 98° C., 30 sec-annealing at 60° C. and 30 sec-extension at 72° C. The PCR products were separated (20 µl) by electrophoresis in a 3% agarose gel stained with ethidium bromide and visualized under UV lights. No template (NTC) reactions were used as negative control. The final confirmation of identity of these products was carried out by Sanger sequencing to establish that the correct and expected exon junctions have been maintained.

Results

AON-Induced Modification on the Abca4 mRNA in Mouse Photoreceptors

We have designed a 2'-OMePS AON to interfere with the splicing of the pre-mRNA of the photoreceptor-specific Abca4 gene (Molday et al., 2000). Using the mfold software and ESEfinder program (for details see: Gerard et al., 2012), we designed an AON targeting exon 10. Since no photoreceptor cell line is available in the laboratory, we proceeded to intravitreal injections of 10 nmol of 2'-OMePS AON into the vitreous of the left eye of C57BL/6J mice without prior in-vitro validation. Mice were sacrificed at 2, 6 and 10 days post-injection and the retinas of both injected and non-injected eyes were prepared as previous. Skipping was analyzed by RT-PCR analysis using primers designed in exon 9 (Forward) and exon 11 (Reverse), respectively. Agarose gel electrophoresis supported successful skipping in all treated eyes with the apparition of a shorter PCR product absent in non-treated eyes (FIG. 5) which was confirmed by Sanger sequencing.

TABLE A

Selection of monogenic pathologies for which a modulation of alternate splicing, leading to a shift in ratio of isoforms, may bear therapeutic consequences.

| Gene | Nb exons | Disease | Description |
| --- | --- | --- | --- |
| ABCA4 | 50 | ARMD2 | age related macular dystrophy 2 (heterozygous ABCA4 defect), see also STGD1 |
|  |  | CORD4 | cone-rod dystrophy 4, characterized by initial loss of visual acuity and macular chorioretinal atrophy, followed by a constriction of the peripheral visual field |
|  |  | RP19 | retinitis pigmentosa 19, retinal rod-cone dystrophy, autosomal recessive characterized by initial night blindness in the first decade, followed by a decrease of visual acuity in the 2nd decade with distinctive features of choriocapillaris atrophy |
|  |  | STGD1 | Stargardt disease, juvenile, macular dystrophy 1, autosomal recessive, characterized by decreased central vision, atrophy of the macula and underlying retinal pigment epithelium and frequent yellow "flavimaculatus flecks" in the posterior pole of the retina, including late onset fundus flavimaculatus |
| AIPL1 | 6 | CORD3 | retinal cone-rod dystrophy 3 |
|  |  | LCA4 | Leber congenital amaurosis type 4, autosomal recessive, characterized by congenital non evolutive blindness, with pendular nystagmus, anterior keratoconus, roving eye movements, absent ocular pursuit and eye poking, severe photophobia, hypermetropia, normal fundus at birth followed by salt and pepper aspect of retina and typical RP, non recordable ERG |
| APC | 15 | CHRPE | retinal pigment epithelium, congenital hypertrophy, Gardner syndrome including Turcot's syndrome (with association to malignant tumor of the CNS) |
| CDH23 | 13 | USH1D | Usher syndrome type ID, characterized by profound congenital neurosensory deafness, constant vestibular dysfunction and retinitis pigmentosa of prepubertal onset, leading to blindness |
| COL11A1 | 66 | AOM2 | Stickler syndrome 2, autosomal dominant, characterized by a membranous or type 1 vitreous phenotype associated with congenital myopia, midline clefting, a flattened mid-facial appearance, neurosensory deafness and joint hypermobility and a degenerative arthropathy, later in life (arthroophthalmopathy,) |
|  |  | MRSH | Marshall syndrome characterized by midface hypoplasia, saddle nose, myopia, early-onset cataract, neurosensory |

TABLE A-continued

Selection of monogenic pathologies for which a modulation of alternate splicing, leading to a shift in ratio of isoforms, may bear therapeutic consequences.

| Gene | Nb exons | Disease | Description |
|---|---|---|---|
| CRB1 | 11 | LCA8 | deafness progressive, predominantly cochlear without defective morphogenesis of the osseous labyrinthe, short stature Leber congenital amaurosis type 8, autosomal recessive, characterized by congenital non evolutive blindness, with pendular nystagmus, anterior keratoconus, roving eye movements, absent ocular pursuit and eye poking, severe photophobia, hypermetropia, normal fundus at birth followed by salt and pepper aspect of retina and typical RP, non recordable ERG |
|  |  | RP12 | retinitis pigmentosa 12, autosomal recessive, early onset, with para-arteriolar preservation of the RPE |
| DMD | 86 | OED | blindness, night, congenital, stationary 2, some incomplete forms, with persistence of slight rod function (dystrophin defect) |
| EYA1 | 16 | ASMD4 | ocular anterior segment mesenchymal dysgenesis 4, including Peters anomaly and congenital cataract, autosomal dominant |
| GUCY2D | 20 | CORD6 | retinal cone rod dystrophy 6, characterized by initial loss of visual acuity and abnormal color vision, followed by night blindness and peripheral visual field loss |
|  |  | LCA1 | Leber congenital amaurosis type 1, autosomal recessive, characterized by congenital non evolutive blindness, with pendular nystagmus, roving eye movements, absent ocular pursuit and eye poking, severe photophobia and hypermetropia, normal fundus at birth followed by salt and pepper aspect of retina and typical RP, non recordable ERG |
| LCAT | 6 | FED | dyslipoproteinemic corneal dystrophy, Fish-Eye disease |
|  |  | LCAT | hypercholesterolemia, unesterified, characterized by corneal opacities, target cell hemolytic anemia, proteinuria with renal failure, Norum disease including susceptibility to familial combined hyperlipemia and premature coronary artery disease |
| MYO7A | 49 | USH1B | Usher syndrome, type IB, autosomal recessive, characterized by profound congenital neurosensory deafness, constant vestibular dysfunction and retinitis pigmentosa of prepubertal onset leading to blindness (see DFNB2) |
| NDP | 3 | COATS | Coats syndrome, characterized by abnormal retinal development (retinal telangiectasia) which results in massive subretinal lipid accumulation (exudative retinal detachment), almost invariably isolated, unilateral and seen in males, a female with a variant giving birth to a son affected with Norrie disease |
|  |  | EVR2 | vitreoretinopathy, exudative, rare X-linked form (allelic to NDP, may be involving a linked gene in rare cases) |
|  |  | NDP | Norrie disease (pseudoglioma), characterized by congenital retinal dysplasia, mental retardation and deafness |
| NPHP1 | 4?20? | SLSN1 | Senior-Loken syndrome 1, juvenile nephronophtisis with retinal dystrophy different from Leber congenital amaurosis |
| PANK2 | 8 | HARP | hypoprebetalipoproteinemia, acanthocytosis, retinitis pigmentosa and pallidal degeneration |
|  |  | PANK2 | Hallervorden-Spatz disease, with progressive rigidity dystonia, retinitis pigmentosa, brain iron accumulation, including forms with extensive accumulation of both tau and alpha-synuclein . HARP syndrome characterized by hypoprebetalipoproteinemia, acanthocytosis, retinitis pigmentosa, and pallidal degeneration |
| PAX6 | 14 | AN | aniridia, homologous to mouse small eye, Drosophila eyeless, also including atypical phenotypes such as ocular coloboma as well as anophthalmia, foveal hypoplasia and central nervous system defect in compound heterozygotes |
|  |  | ASMD3 | ocular anterior segment mesenchymal dysgenesis 3, including Peters anomaly, Axenfeld anomaly, corneal dystrophy associated with congenital cataract, autosomal dominant |
|  |  | ECTP | ectopia pupillae |
|  |  | FVH | foveal hypoplasia, isolated |
|  |  | OPNAB | optic nerve hypoplasia and aplasia, bilateral, including Morning glory disc anomaly |
|  |  | WAGR | contiguous gene syndrome characterized by predisposition to nephroblastoma (Wilms tumor), aniridia, genitourinary abnormalities, mental retardation |
| PDE6B | 22 | ARRP2 | retinitis pigmentosa, autosomal recessive 2 (PDE6B), mouse rd homolog |
|  |  | CSNB3 | blindness, night, congenital, stationary 3, autosomal dominant |
| PEX7 | 10 | PBD7 | Refsum disease, phytanic acid oxidase deficiency, hereditary motor and sensory neuropathy 4 with ataxia, retinitis pigmentosa, and polyneuropathy , complementation group 11 or R |

TABLE A-continued

Selection of monogenic pathologies for which a modulation of alternate splicing, leading to a shift in ratio of isoforms, may bear therapeutic consequences.

| Gene | Nb exons | Disease | Description |
|---|---|---|---|
| PITX2 | 3 | IHG2 | autosomal dominant iris hypoplasia, with goniodysgenesis (iridogoniodysgenesis) elevated intraocular pressure and secundary glaucoma (see RIEG1) |
| | | RIEG1 | ocular anterior segment mesenchymal dysgenesis, Axenfeld Rieger syndrome , including posterior embryotoxon, iris stromal hypoplasia and abnormalities of pupil shape (corectopia) and number (polycoria) and secundary glaucoma associated with other anomalies, most frequently anodontia/hypodontia, maxillary hypoplasia, umbilical hernia due a failure of involution of periumbilical skin, see also IHG2 |
| RDS | 3 | MDBS1 | macular dystrophy, autosomal dominant, butterfly shaped pigmentary macular dystrophy 1, including Zermatt macular dystrophy, retinitis pigmentosa with bull's-eye maculopathy and other pattern dystrophies |
| | | RP7 | retinitis pigmentosa 7, including retinitis punctata albescens |
| RHO | 5 | ARRP1 | retinitis pigmentosa 1, autosomal recessive 1 |
| | | CSNB6 | blindness, night, congenital, stationary 6, autosomal dominant |
| | | RP4 | retinitis pigmentosa 4, autosomal dominant, type I and others, including some retinitis punctata albescens, the first most common ADRP locus (20-31%) |
| RLBP1 | 9 | ARRP7 | retinitis pigmentosa, autosomal recessive 8, early onset, with optic disc atrophy and macular degeneration |
| | | NFRCD | news foundland rod-cone dystrophy, early onset retinal dystrophy, severe, with precoce blindness |
| | | RPALB | retinitis punctata albescens, characterized by congenital stationary night blindness and abnormally slow regeneration of visual pigments with uniform white-yellow dots scattered through retina, autosomal recessive, including Bothnia dystrophy (high prevalence in Northern Sweden) |
| RPE65 | 14 | LCA2 | Leber congenital amaurosis type 2, autosomal recessive, characterized by congenital blindness with pendular nystagmus, roving eye movements, absent ocular pursuit and eye poking, night blindness, normal fundus at birth followed by salt and pepper aspect of retina and typical aspect of RP, non recordable ERG, presenting a transient improvement during evolution |
| | | RP20 | variable expression retinal dystrophy, childhood-onset, autosomal recessive 8, affecting rod and cone photoreceptors |
| RPGR | 19 | CORDX1 | cone-rod dystrophy, 1 (RP2 and RP3 excluded), progressive retinal degeneration, characterized by progressive photophobia, decreased central vision and dyschromatopsia |
| | | MDXA1 | X-linked recessive atrophic macular degeneration |
| | | RP15 | retinitis pigmentosa 15, X-linked dominant, characterized by initial loss of visual acuity and color vision followed by night blindness and peripheral visual field loss (see OMIM 300029) |
| | | RP3 | retinitis pigmentosa 3, X-linked recessive form of choroidoretinal degeneration which is distinguished from other types by the presence in heterozygous women of a tapetal-like retinal reflex, including retinitis pigmentosa with recurrent respiratory infections |
| TULP1 | 14 | LCA10 | Leber congenital amaurosis type 10, autosomal recessive, with nystagmus, night blindness profound visual deficiency, without hypermetropia, rod cone dystrophy |
| | | RP14 | retinitis pigmentosa, autosomal recessive 4, severe, early onset, characterized by nystagmus, diminished visual acuity color vision disturbances, bull's eye maculopathy and peripheral pigmentary retinopathy, associated with an unrecordable ERG |
| USH2A | 21 | ARRP15 | retinitis pigmentosa autosomal recessive 15, non syndromic |
| | | USH2A | Usher syndrome, type IIA, autosomal recessive, congenital, moderate to severe neurosensory deafness, progressive with age, normal vestibular function and retinitis pigmentosa, exhibiting phenotypic variation, including atypical cases with vestibular dysfunction, including cases of non syndromic retinitis pigmentosa |

REFERENCES

Throughout this application, various references describe the state of the art to which this invention pertains. The disclosures of these references are hereby incorporated by reference into the present disclosure.

The invention claimed is:

1. A method for performing antisense oligonucleotide-mediated exon skipping of a gene encoding ABCA4 in a photoreceptor cell of a subject in need thereof comprising the step of injecting into the vitreous of the subject an amount of a naked antisense oligonucleotide targeting the gene encoding ABCA4, wherein the subject suffers from Stargardt disease caused by a mutation which modifies the splicing and/or creates a premature termination in the ABCA4 gene important to the functioning and/or the survival of the photoreceptor cell, wherein the antisense oligonucleotide comprises a sequence that is complementary to a splice donor site, splice acceptor site, or a branch site within the pre-mRNA of the ABCA4 gene, wherein the naked antisense oligonucleotide performs antisense oligonucleotide-mediated exon skipping in the pre-mRNA from the ABCA4 gene which mutation causes Stargardt disease, in the nucleus of the photoreceptor cell of the subject, and wherein the antisense oligonucleotide is chronically administered by intravitreal injections at least 10 days apart.

2. The method of claim 1 wherein the naked antisense oligonucleotide is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, U7- or U1-mediated antisense oligonucleotides, peptide-conjugated, nanoparticle-complexed antisense oligonucleotides, 2'-O-Me RNA/ENA chimera oligonucleotides, and 2'-O-methyl-phosphorothioate oligonucleotides.

3. The method of claim 1, wherein the antisense oligonucleotide is 10-50 nucleotides in length.

4. The method of claim 1, wherein the antisense oligonucleotide is chronically administered by intravitreal injections at least one month apart.

5. A method of treating Stargardt disease caused by a mutation which modifies the splicing and/or creates a premature termination in the ABCA4 gene, important to the functioning and/or the survival of a photoreceptor cell, in a subject in need thereof, comprising the step of injecting into the vitreous of the subject an amount of a naked antisense oligonucleotide targeting a gene encoding ABCA4, wherein the antisense oligonucleotide comprises a sequence that is complementary to a splice donor site, splice acceptor site, or a branch site within the pre-mRNA of the ABCA4 gene, wherein the naked antisense oligonucleotide performs antisense oligonucleotide-mediated exon skipping in the pre-mRNA from the ABCA4 gene which mutation causes Stargardt disease in the nucleus of a photoreceptor cell of the subject, and wherein the antisense oligonucleotide is chronically administered by intravitreal injections at least 10 days apart.

6. The method of claim 5, wherein the naked antisense oligonucleotide performs antisense oligonucleotide-mediated exon skipping in the nucleus of a photoreceptor cell of the subject.

7. The method of claim 5, wherein the naked antisense oligonucleotide is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, U7- or U1-mediated antisense oligonucleotides, peptide-conjugated, nanoparticle-complexed antisense oligonucleotides, 2'-O-Me RNA/ENA chimera oligonucleotides, and 2'-O-methyl-phosphorothioate oligonucleotides.

8. The method of claim 5, wherein the antisense oligonucleotide is 10-50 nucleotides in length.

9. The method of claim 5, wherein the antisense oligonucleotide is chronically administered by intravitreal injections at least one month apart.

\* \* \* \* \*

SEQUENCE LISTING

<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: Synthetic primer

<400> SEQUENCE: 1
gaccaccttg agaaggaaac                                                  20

<210> SEQ ID NO 2
<211> LENGTH: 19
<212> TYPE: DNA
<213> ORGANISM: Artificial
<220> FEATURE:
<223> OTHER INFORMATION: Synthetic primer

<400> SEQUENCE: 2
catcctgctc agcttgatc                                                   19

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
cccaccaaac tattgccaac                                                  20

<210> SEQ ID NO 4
<211> LENGTH: 22
<212> TYPE: DNA
<213> ORGANISM: Artificial
<220> FEATURE:
<223> OTHER INFORMATION: Synthetic primer

<400> SEQUENCE: 4
gagagtcatc ttgttctgct ac                                               22

<210> SEQ ID NO 5
<211> LENGTH: 26
<212> TYPE: DNA
<213> ORGANISM: Artificial
<220> FEATURE:
<223> OTHER INFORMATION: Synthetic primer

<400> SEQUENCE: 5
tgactgctaa gtacagggac atcttg                                           26

<210> SEQ ID NO 6
<211> LENGTH: 24
<212> TYPE: DNA
<213> ORGANISM: Artificial
<220> FEATURE:
<223> OTHER INFORMATION: Synthetic primer

<400> SEQUENCE: 6
aggagatgtt ttcacactcc aggt                                             24

<210> SEQ ID NO 7
<211> LENGTH: 23
<212> TYPE: DNA
<213> ORGANISM: Artificial

```
<220> FEATURE:
<223> OTHER INFORMATION: Synthetic primer

<400> SEQUENCE: 7
ctggccccag ttgtaatttg tga                                           23

<210> SEQ ID NO 8
<211> LENGTH: 24
<212> TYPE: DNA
<213> ORGANISM: Artificial
<220> FEATURE:
<223> OTHER INFORMATION: Synthetic primer

<400> SEQUENCE: 8
ctgttcccag gcttgttcaa tagt                                          24

<210> SEQ ID NO 9
<211> LENGTH: 24
<212> TYPE: DNA
<213> ORGANISM: Artificial
<220> FEATURE:
<223> OTHER INFORMATION: Synthetic primer

<400> SEQUENCE: 9
tgactgctaa gtacagggac atct                                          24

<210> SEQ ID NO 10
<211> LENGTH: 24
<212> TYPE: DNA
<213> ORGANISM: Artificial
<220> FEATURE:
<223> OTHER INFORMATION: Synthetic primer

<400> SEQUENCE: 10
aggagatgtt ttcacactcc aggt                                          24

<210> SEQ ID NO 11
<211> LENGTH: 23
<212> TYPE: DNA
<213> ORGANISM: Artificial
<220> FEATURE:
<223> OTHER INFORMATION: Synthetic primer

<400> SEQUENCE: 11
ctggccccag ttgtaatttg tga                                           23

<210> SEQ ID NO 12
<211> LENGTH: 24
<212> TYPE: DNA
<213> ORGANISM: Artificial
<220> FEATURE:
<223> OTHER INFORMATION: Synthetic primer

<400> SEQUENCE: 12
ctgttcccag gcttgttcaa tagt                                          24

<210> SEQ ID NO 13
<211> LENGTH: 25
<212> TYPE: DNA
<213> ORGANISM: Artificial
<220> FEATURE:
<223> OTHER INFORMATION: Synthetic primer

<400> SEQUENCE: 13
tgacctaaag accattgcac ttcgt                                         25
```

```
<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
ctgcagcaaa tcgcttggga                                                 20

<210> SEQ ID NO 15
<211> LENGTH: 25
<212> TYPE: DNA
<213> ORGANISM: Artificial
<220> FEATURE:
<223> OTHER INFORMATION: Synthetic primer

<400> SEQUENCE: 15
cctgtatgct atccagaaaa cccct                                           25

<210> SEQ ID NO 16
<211> LENGTH: 25
<212> TYPE: DNA
<213> ORGANISM: Artificial
<220> FEATURE:
<223> OTHER INFORMATION: Synthetic primer

<400> SEQUENCE: 16
cgtagcagtt cagtatgttc ggctt                                           25

<210> SEQ ID NO 17
<211> LENGTH: 22
<212> TYPE: DNA
<213> ORGANISM: Artificial
<220> FEATURE:
<223> OTHER INFORMATION: Synthetic primer

<400> SEQUENCE: 17
ctgcggttgt gatgtggtct gt                                              22

<210> SEQ ID NO 18
<211> LENGTH: 24
<212> TYPE: DNA
<213> ORGANISM: Artificial
<220> FEATURE:
<223> OTHER INFORMATION: Synthetic primer

<400> SEQUENCE: 18
tgtgggtgat cagcgtctta aagt                                            24

<210> SEQ ID NO 19
<211> LENGTH: 24
<212> TYPE: DNA
<213> ORGANISM: Artificial
<220> FEATURE:
<223> OTHER INFORMATION: Synthetic primer

<400> SEQUENCE: 19
gttggataca ggccagactt tgtt                                            24

<210> SEQ ID NO 20
<211> LENGTH: 25
<212> TYPE: DNA
<213> ORGANISM: Artificial
<220> FEATURE:
<223> OTHER INFORMATION: Synthetic primer
```

<400> SEQUENCE: 20
aaacgtgatt caaatccctg aagta                                          25

<210> SEQ ID NO 21
<211> LENGTH: 22
<212> TYPE: DNA
<213> ORGANISM: Artificial
<220> FEATURE:
<223> OTHER INFORMATION: Synthetic primer

<400> SEQUENCE: 21
ccaaacacaa acggttccca gt                                             22

<210> SEQ ID NO 22
<211> LENGTH: 20
<212> TYPE: DNA
<213> ORGANISM: Artificial
<220> FEATURE:
<223> OTHER INFORMATION: Synthetic primer

<400> SEQUENCE: 22
gcttgccatc cagccattca                                                20

<210> SEQ ID NO 23
<211> LENGTH: 25
<212> TYPE: DNA
<213> ORGANISM: Artificial
<220> FEATURE:
<223> OTHER INFORMATION: Synthetic primer

<400> SEQUENCE: 23
gggacagtga gtacccagac atcta                                          25

<210> SEQ ID NO 24
<211> LENGTH: 22
<212> TYPE: DNA
<213> ORGANISM: Artificial
<220> FEATURE:
<223> OTHER INFORMATION: Synthetic primer

<400> SEQUENCE: 24
ccagacttgg tgttggatgc tt                                             22

<210> SEQ ID NO 25
<211> LENGTH: 28
<212> TYPE: DNA
<213> ORGANISM: Artificial
<220> FEATURE:
<223> OTHER INFORMATION: Synthetic antisense oligonucleotide

<400> SEQUENCE: 25
caaagaagta ccagatctgg ggccctac                                       28

<210> SEQ ID NO 26
<211> LENGTH: 21
<212> TYPE: DNA
<213> ORGANISM: Artificial
<220> FEATURE:
<223> OTHER INFORMATION: Synthetic primer

<400> SEQUENCE: 26
tgatccagag cctggagtca a                                              21

<210> SEQ ID NO 27

```
<211> LENGTH: 21
<212> TYPE: DNA
<213> ORGANISM: Artificial
<220> FEATURE:
<223> OTHER INFORMATION: Synthetic primer

<400> SEQUENCE: 27
ttcttctccg agctgcctat t                                              21

<210> SEQ ID NO 28
<211> LENGTH: 30
<212> TYPE: RNA
<213> ORGANISM: Artificial Sequence
<220> FEATURE:
<223> OTHER INFORMATION: m23D

<400> SEQUENCE: 28
guuuucaaaa uauaaauacc uuagguauuc                                     30

<210> SEQ ID NO 29
<211> LENGTH: 20
<212> TYPE: RNA
<213> ORGANISM: Artificial Sequence
<220> FEATURE:
<223> OTHER INFORMATION: m23ESE

<400> SEQUENCE: 29
gaugacgaau cacugcaaac                                                20

<210> SEQ ID NO 30
<211> LENGTH: 24
<212> TYPE: RNA
<213> ORGANISM: Artificial Sequence
<220> FEATURE:
<223> OTHER INFORMATION: m36D

<400> SEQUENCE: 30
guucucagaa ucuuaccuga gcug                                           24

<210> SEQ ID NO 31
<211> LENGTH: 20
<212> TYPE: RNA
<213> ORGANISM: Artificial Sequence
<220> FEATURE:
<223> OTHER INFORMATION: m36ESE

<400> SEQUENCE: 31
caugaagguc uuccucaugc                                                20

<210> SEQ ID NO 32
<211> LENGTH: 20
<212> TYPE: RNA
<213> ORGANISM: Artificial Sequence
<220> FEATURE:
<223> OTHER INFORMATION: m23ESEsense

<400> SEQUENCE: 32
guuugcagug auucgucauc                                                20
```